United States Patent [19]

Marsden et al.

[11] Patent Number: 4,626,560
[45] Date of Patent: Dec. 2, 1986

[54] NOVEL BINDING AGENT COMPOSITIONS, FOUNDRY SAND COMPOSITIONS AND UREIDO FUNCTIONAL ORGANOSILICON COMPOUNDS

[75] Inventors: James G. Marsden; Enrico J. Pepe, both of Amawalk, N.Y.

[73] Assignee: Union Carbide Corporation, Danbury, Conn.

[21] Appl. No.: 534,165

[22] Filed: Sep. 21, 1983

Related U.S. Application Data

[62] Division of Ser. No. 309,657, Oct. 8, 1981, abandoned.

[51] Int. Cl.$^4$ .................. C08K 9/06; C08K 3/34; B22C 11/22
[52] U.S. Cl. ............................ 523/145; 523/208; 523/213
[58] Field of Search .............. 556/421; 260/384.41; 523/145, 208, 213

[56] References Cited

U.S. PATENT DOCUMENTS

| | | | |
|---|---|---|---|
| 3,455,725 | 7/1969 | Jex et al. | 525/476 |
| 3,506,701 | 4/1970 | Di Paola | 528/24 |
| 3,650,814 | 3/1972 | Elder | 428/405 |
| 3,671,562 | 6/1972 | Pepe et al. | 525/342 |
| 3,676,478 | 7/1972 | Golitz et al. | 556/420 |
| 3,726,907 | 4/1973 | Tesoro et al. | 528/10 |
| 3,745,139 | 7/1973 | Kachur et al. | 523/139 |
| 3,754,971 | 8/1973 | Pepe et al. | 523/217 |
| 3,772,351 | 11/1973 | Krahnke | 528/28 |
| 3,847,860 | 11/1974 | Seiler et al. | 524/262 |
| 4,046,794 | 9/1977 | Pepe et al. | 528/25 |
| 4,083,817 | 4/1978 | Anderson | 523/144 |
| 4,111,253 | 9/1978 | Epstein et al. | 524/596 |
| 4,124,556 | 11/1978 | Schafer et al. | 524/114 |
| 4,193,909 | 3/1980 | Lundberg et al. | 523/123 |
| 4,256,623 | 3/1981 | Juenger et al. | 524/262 |
| 4,268,425 | 5/1981 | Gardikes | 523/143 |
| 4,271,229 | 6/1981 | Temple | 524/188 |

FOREIGN PATENT DOCUMENTS

| | | |
|---|---|---|
| 1252853 | 4/1968 | Fed. Rep. of Germany . |
| 4818 | 1/1979 | Japan . |

*Primary Examiner*—Herbert J. Lilling
*Attorney, Agent, or Firm*—Paul W. Leuzzi

[57] ABSTRACT

Binding agent compositions for inorganic fillers or oxides containing a curable binder such as a hardenable resin, and a ureido-functional organosilicon compound as described. Foundry sand compositions including binding agent compositions as described, sand and a catalyst for the hardenable resin. Shaped products comprising inorganic oxide particles, e.g., sand, a binding agent composition as described and catalyst for the hardenable resin wherein the hardenable resin is in its hardened form. Novel ureido-functional organosilicon compounds having two hydrolyzable or hydroxy groups to the molecule and at least one ureido-functional group in which the ureido group is connected to silicon by means of a group containing at least five carbon atoms.

9 Claims, No Drawings

NOVEL BINDING AGENT COMPOSITIONS, FOUNDRY SAND COMPOSITIONS AND UREIDO FUNCTIONAL ORGANOSILICON COMPOUNDS

This application is a division of prior U.S. application Ser. No. 309,657, filed Oct. 8, 1981, now abandoned.

BACKGROUND OF THE INVENTION

1. Field of the Invention

This invention relates to binding agent compositions having especially good shelf life which can be used with inorganic fillers or oxides, such as foundry sand, for the purpose of imparting improved strength to shapes, such as foundry molds or cores, made therefrom. The invention also relates to inorganic oxide compositions, such as foundry sand compositions, containing the inorganic oxide, the improved binding agent composition and catalysts for said binding agent. The invention also relates to certain novel ureido-functional organosilicon compounds having use in binding agent compositions for foundry sands.

2. Description Of The Prior Art

It is well known in the art that one can impart general improved strengths and increased humidity resistance to foundry cores by adding a silane compound to the resinous foundry binder used to form the cores. Foundry cores made with such resinous binders as phenolic/isocyanate systems, furan systems, oil modified polyol/polyisocyanate systems, phenolic resins and urea/phenolic resins have a tendency to lose strength and become weak upon exposure to humid conditions. As illustrated by U.S. Pat. Nos. 3,409,579 and 3,403,721, silane compounds have been added to such resinous binders to increase the humidity resistance and general strength of foundry cores made with these binders. Aqueous dispersions of silane compounds have also been used as binders themselves (see U.S. Pat. No. 3,093,494).

It is known that aminoalkyl trialkoxysilanes, such as γ-aminopropyltrimethoxysilane, improve the adherence of thermosetting resins to inorganic oxide materials. It is furthermore known that these aminosilanes can be mixed with thermosetting phenolic resins and then the resulting mixtures can be mixed directly with sands or other inorganic oxide material to be shaped and solidified (cf. DE-AS No. 1,252,853 and DE-PS No. 1,494,381).

The use of N-(aminoalkyl)-aminoalkylsilanes as adhesion improvers between thermosetting resins and inorganic oxide material is also known. These compounds are used in the same manner as the above-mentioned aminosilanes in which there is no substitution on the nitrogen atom (cf. U.S. Pat. No. 3,234,159).

Both the aminoalkylsilanes which are not substituted on the nitrogen atom and those which are substituted by aminoalkyl groups, all of which are referred to hereinafter as aminosilanes, improve the adhesion of thermosetting phenolic resins to inorganic oxide substances to virtually the same degree when they are mixed with the resins. This improvement of adhesion, however, diminishes in the course of time if these aminosilane-containing resins are stored for a relatively long time at room temperature. U.S. Pat. No. 4,256,623 reports that, after standing for only 14 days, for example, the adhesion-improving action of aminosilanes declines by about 40%, and at the end of only a month the adhesiviting effect produced by γ-aminopropyltriethoxysilane in phenolic resin has been reduced by one half.

It has been further reported that the loss of the adhesivizing action of the aminosilane in mixture with thermosetting resins is probably due to a decomposition of these silanes in the resins. Therefore, there existed the problem of finding an adhesivizing agent which, when mixed with thermosetting resins, decomposes very slightly or not at all, and produces its adhesivizing action to the same or an only slightly lesser extent, even after the resin has been stored for a relatively long time and which therefore will be useful in the preparation of binding agents for inorganic oxide materials such as, for example, foundry sands, such binding agents being made from ureido-functional silanated phenolic resins whose strength enhancing effectiveness will remain unaltered or only slightly reduced, even after a relatively long period of storage.

U.S. Pat. Nos. 3,671,562; 3,754,971 and 4,046,794 disclose ureido-functional organosilicon compounds and the use of same as coupling agents on inorganic substrates such as glass, clay, silica, hydrated silica, fumed silica, sand, e.g., foundry sand and the like. These patents fail to disclose or suggest the binding agent compositions or the foundry sand compositions disclosed and claimed herein and also fail to disclose or suggest the ureido-functional organosilicon compounds claimed herein.

In general, organofunctional silanes are widely used as additives to polymerizable resins to provide improved adhesion of the resin to substrates and to improve the physical properties of composites prepared from the resin and fibrous and/or particulate materials. A specific application of this general use is the addition of organofunctional silicon compounds to hardenable resin compositions used as binders for sand to form molds and cores for use in casting metal articles. It is important in this use that the improvement in properties, provided by adding an organofunctional silicon compound, be stable in respect to the age of the organofunctional silicon compound/resin mixture.

SUMMARY OF THE INVENTION

This invention is concerned with the discovery that certain ureido-functional silicon compounds have novel and unexpected properties when employed as additives for the curable binder. It has been found, quite unexpectedly, that the use of ureido-functional silicon compounds that contain two hydrolyzable groups to the molecule provide significantly greater performance stability, when added to a curable binder, such as, a hardenable resin, than that provided by a corresponding ureido-functional silicon compound that contains three hydrolyzable groups. Ureido-functional silicon compounds containing three hydrolyzable groups are useful additives for curable binders, such as, hardenable resins, and, in fact, are used commercially; however, the improvements in properties provided by the use of such compounds decrease with the time that the compound is in contact with the resin. The use of similar ureido-functional silicon compounds, but having two hydrolyzable groups, pursuant to this invention, yield a significant increase in performance stability.

More particularly, this invention relates to binding agent compositions for inorganic fillers or oxides comprising a curable binder such as a hardenable resin mixed with a ureido-functional organosilicon compound having:

(a) at least one silicon-bonded ureido group of the formula $$[R_2'NC(O)]_n R— \quad (I)$$

wherein R is an aliphatic radical containing nitrogen, hydrogen and at least three carbon atoms wherein at least one nitrogen atom therein is bonded to each $[R_2'NC(O)]$— to form $$(R_2'NCON<),$$

at least one free valence of $$(R_2'NCON<)$$

is bonded to an alkylene carbon atom of R, any other free valence of $$(R_2'NCON<)$$

is bonded to a member selected from the group consisting of hydrogen, alkyl, aryl, cycloalkyl and aralkyl, any nitrogen atom in R is separated from silicon by at least three sequentially joined carbon atoms, R' is hydrogen, alkyl of 1 to 8 carbon atoms or a methylol group, preferably at least one R' group is hydrogen, most preferably both R' groups are hydrogen.

(b) two silicon-bonded hydroxyl groups or hydrolyzable or condensible groups selected from the class consisting of alkoxy, acyloxy, aryloxy, amino and haloalkoxy; and (c) any remaining free valence of silicon being bonded (1) to oxygen which in turn is bonded to another silicon atom to form therewith a siloxane or (2), to hydrogen or, by carbon to silicon bonds, to a monovalent organic group selected from the group consisting of alkyl, acyl, cycloalkyl, aryl, alkaryl, aralkyl, alkenyl, alkadienyl, cycloalkenyl, haloalkyl, halocycloalkyl, cyanoalkyl, cyanoaryl, cyanocycloalkyl, carboxyalkyl, carboxyaryl, carboxycycloalkyl, isocyanatoaryl, isocyanatocycloalkyl, alkyl carboxyalkyl, aryl carboxyalkyl, hydroxyalkyl, hydroxy(polyalkyleneoxy)alkyl, alkenoyloxyalkyl, epoxyalkyl, epoxyalkyloxyalkyl, aminoaryl and aminoalkyl. The ureido-functional organosilicon compounds used in this invention preferably contain 1 to 10 silicon atoms. The novel ureido-functional organosilicon compounds of this invention are as described above wherein R as shown in formula I contains at least 5 carbon atoms.

Preferably the ureido-functional organosilicon compound is a silane having the average formula:

$$[(R_2'NC(O)]_n R]_a Si(R'')_{2-a} X_2 \quad (II)$$

wherein R, R' and n are as defined hereinabove, R'' is hydrogen or a monovalent organic group bonded to silicon by a carbon to silicon bond, selected from the group consisting of alkyl, acyl, cycloalkyl, aryl, alkaryl, aralkyl, alkenyl, alkadienyl, cycloalkenyl, haloalkyl, halocycloalkyl, cyanoalkyl, cyanoaryl, cyanocycloalkyl, carboxyalkyl, carboxyaryl, carboxycycloalkyl, isocyanatoaryl, isocyanatocycloalkyl, alkyl carboxyalkyl, aryl carboxyalkyl, hydroxyalkyl, hydroxy(polyalkyleneoxy)alkyl, alkenoyloxyalkyl, epoxyalkyl, epoxyalkyloxyalkyl, aminoaryl and aminoalkyl; X is hydroxyl or a hydrolyzable or condensible radical, selected from the group consisting of hydroxyl, alkoxy, acyloxy, aryloxy, amino and haloalkoxy; and a is an integer of 1 or 2. The novel ureido-functional organosilanes of this invention are those of formula II wherein R contains at least five carbon atoms. Specific examples of ureido-functional organosilanes are, $NH_2C(O)NH(CH_2)_2NH(CH_2)_3Si(Me)(OMe)_2$;

$NH_2C(O)NHCH_2CH(CH_3)(CH_2)_2Si(Me)(OEt)_2$;

$NH_2C(O)NH(CH_2)_2N[C(O)NH_2](CH_2)_3Si(Me)(OMe)_2$;

$NH_2C(O)NH(CH_2)_3Si(Et)(OMe)_2$;

$MeO(Me)Si(CH_2)_3NHC(O)NH(CH_2)_3Si(Me)(OMe)_2$;

$NH_2C(O)NHC_2H_4NHC_2H_4NHC_3H_6Si(Me)(OEt)_2$;

Ti $NH_2C(O)NH(CH_2)_2N[C(O)NH_2](CH_2)_2NH(CH_2)_3Si(Et)(GMe)_2$;

$NH_2C(O)NH(CH_2)_2N[C(O)NH_2](CH_2)_2N[C(O)NH_2](CH_2)_3Si(Et)(OEt)_2$;

$NH_2C(O)NH(CH_2)_4SiEt(OMe)_2$; and $NH_2C(O)NH(CH_2)_4Si(C_6H_5)(OEt)_2$.

Included in the ureido-functional organosilicon compounds illustrated by formula I are relatively low molecular weight siloxanes, e.g., having 2 to 10 silicon atoms interconnected by silicon-bonded oxygen atoms forming ≡SiOSi≡ linkages. Ureido-functional organosiloxanes of this type have, per molecule, two silicon-bonded hydroxyl groups or two silicon-bonded hydrolyzable or condensible groups as defined above and at least one silicon-bonded group of the formula $$[R_2'NC(O)]_n R—$$

as defined in formula I and any remaining free valence of silicon is bonded to oxygen which in turn is bonded to another silicon atom to form therewith the siloxane, or, to hydrogen, or, by carbon to silicon bonds, to a monovalent organic group as defined above. The preferred ureido-functional organosiloxanes include the disiloxanes, trisiloxanes, tetrasiloxanes such as the cyclic tetramer, and the pentasiloxanes.

Typical monovalent organic groups bonded to silicon in the ureido-functional organosilicon compounds described above including R'' in the formula II include alkyl (e.g., methyl, ethyl, pentyl, dodecyl, octadecyl, 2-ethylhexyl, and the like), cycloalkyl (such as cyclobutyl, cyclohexyl, 4-methylcyclohexyl, and the like), aryl (such as phenyl, 2-naphthyl, 2-anthracyl, biphenyl, and the like), alkaryl (such as 4-methylphenyl, 2,4-diethylphenyl, 4-dodecylphenyl, and the like), aralkyl (such as phenylethyl), alkenyl (such as vinyl, allyl, 3-butenyl, oleyl, and the like), alkadienyl (such as 1-butadienyl-1,4,1-octadecatrienyl-9,11,13-, 1-neoprenyl, and the like), cycloalkenyl (such as 3-cyclohexenyl), haloalkyl (such as chloromethyl, gamma-chloropropyl, 3,3,3-trifluoropropyl, perfluoropropyl, haloaryl (such as 4-chlorophenyl, 2,4-dichlorophenyl, chloronaphthyl), halocycloalkyl (such as 4-chlorocyclohexyl), cyanoalkyl (such as beta-cyanoethyl, gamma-carboxypropyl and the like); cyanoaryl (such as 4-cyanophenyl); cyanocycloalkyl (such as 4-cyanocyclohexyl, 3-cyanocyclopentyl, and the like); carboxyalkyl (such as beta-carboxyethyl, gamma-carboxypropyl, and the like); carboxyaryl (such as 4-carboxyphenyl); carboxycycloalkyl (such as 4-carboxycyclohexyl, 3-carboxycyclopentyl, and the like; isocyanatoalkyl (such as gamma-icocyanatopropyl, delta-isocyanatobutyl, and the like); isocyanatoaryl (such as 4-isocyanatophenyl); isocyanatocycloalkyl (such as 4-isocyanatocyclohexyl); alkyl or aryl carboxyalkyl (such as betamethylcarboxyethyl, gamma-phenyl carboxypropyl, and the like); hydroxyalkyl (such as hydroxymethyl, gamma-hydroxypropyl, and the like; hydroxy(polyalkyleneoxy)alkyl (such as omega-hydroxy(polyethyleneoxy)propyl, and the like); alkenoyloxyalkyl (such as gamma-acrylyoxypropyl, gamma-methacryloxypropyl, and the like; epoxyalkyl (such as 1,2-epoxyethyl, 1,2-epoxypropyl, 1,2-epoxybutyl, and the like; epoxy alkyloxyalkyl (such as glycidyloxypropyl); epoxycycloalkyl (such as beta-3,4-epoxycyclohexylethyl); aminoaryl and aminoalkyl (such as aminomethyl, gamma-aminopropyl, delta-aminobutyl, p-aminophenyl, and the like); and the like.

Typical of the hydrolyzable or condensible groups bonded to silicon in the ureido-functional organosilicon compounds described above including X in formula II include for example alkoxy, e.g., methoxy, ethoxy, propoxy, dodecyloxy, isopropoxy, and the like; aryloxy, e.g., phenoxy, naphthyloxy, biphenyloxy, and the like; alkylamino and arylamino, such as methylamino, diethylamino, phenylamino, and the like; acyloxy, e.g., formyloxy, acetyloxy, propoxy, and the like; any organofunctional radicals such as hydroxyalkoxy, e.g., beta-hydroxyethoxy, gamma-hydroxypropoxy, and the like; hydroxyalkoxyalkoxy, such as beta-hydroxyethoxyethoxy, omega-hydroxy(polyethyleneoxy)ethoxy, omega-hydroxy(poly-1,2-propyleneoxy, and the like; cyanoalkoxy, such as beta-cyanoethoxy, beta-cyanohexoxy and the like; cyanoalkoxyalkoxy, such as beta-cyanoethoxyethoxy, omega-cyanoethoxy(polyethyleneoxy), omega-cyanoethoxy(poly-1,2-propyleneoxy), and the like; carboxyalkoxy, such as beta-carboxyethoxy, beta-carboxyhexoxy and the like; haloalkoxy, such as chloromethoxy, bromoethoxy perfluoropropoxy, and the like; and the like.

The ureido-functional organosilicon compounds used in this invention can be produced by reacting an organocarbamate with an amino-functional organosilicon having:

(a) at least one silicon-bonded group of the formula

 (III)

wherein R, R' and n are as defined in connection with formula I and each R' which is present n times in formula III is bonded to a nitrogen atom of R;

(b) two silicon-bonded hydroxyl groups or hydrolyzable or condensible groups as defined hereinabove; and (c) any remaining free valence of silicon being bonded to (1) oxygen which in turn is bonded to another silicon atom to form therewith a siloxane, or (2) to hydrogen or, by carbon to silicon bonds to a monovalent organic group as described hereinabove. The amino-functional organosilicon compounds used to make the ureido-functional organosilicon compounds employed herein preferably contain 1 to 10 silicon atoms. The amino-functional organosilicon compounds used to make the novel ureido-functional organosilicon compounds of this invention are as described above wherein R as shown in formula III contains at least 5 carbon atoms. Suitable aminofunctional organosilicon compounds useful herein are disclosed in the prior art including U.S. Pat. Nos. 2,971,864, 2,832,754 and 2,942,019 and others, the disclosures of which are incorporated herein by reference. Additional specific examples are gamma-aminopropylmethyldimethoxysilane, N-methyl-gamma-aminopropylmethyldimethoxysilane, N-(gamma-aminopropyl)gamma-aminopropylmethyldimethoxysilane, N-(gamma-aminopropyl)-N-methyl-gamma-aminopropylmethyldimethoxysilane and gamma-aminopropylethyldiethoxysilane, and the like.

Organocarbamates used to produce the ureido-functional organosilicon compounds used in this invention include alkyl, cycloalkyl or aryl carbamates illustrated by methyl carbamate, ethyl carbamate, and n-propyl carbamate, n-butyl carbamate, cyclohexylcarbamate phenyl carbamate, 4-methylphenyl carbamate, 4-dodecyl phenyl carbamate, biphenyl carbamate; and alkylene, cycloalkylene and arylene carbamates, such as ethylene dicarbamate, 1,4-butylene dicarbamate, 1,4-phenylene dicarbamate, 4,4'-bisphenylene dicarbamate, 1,4-cyclohexylene dicarbamate, and the like. The reaction can be carried out neat or in solution or dispersion using solvents or nonsolvents for the silane and/or the carbamate reactants types of solvents and nonsolvents include hydrocarbon solvents, ether solvents, amide solvents, ketone solvents and the like, such as mineral spirits, hexane, n-nonane, benzene, toluene, xylene, methylethyl ketone, methylisobutyl ketone, diethylether, di-n-diisopropyl ether, N,N-dimethyl formamide, and the like. The temperature of the reaction can be relatively low depending upon the reactivity of the carbamate and the amount of amine present in the reaction, usually temperatures in the range of about 40° C. to about 180° C. are satisfactory. Typically a temperature about 50° C. to about 150° C. is more desirable.

This reaction can be operated under atmospheric or subatmospheric pressures. Superatmospheric pressures are employable but are not considered to operate as beneficially as subatmospheric and atmospheric pressures. The reaction product can be separated by distillation, crystallization, decantation, and the like, utilizing standard processing equipment and procedures.

There are other alternative ways known in the art for producing the ureido-functional organosilicon compounds and any suitable procedure can be used. For example, the corresponding isocyanato functional organosilicon compound can be reacted with ammonia to produce the corresponding ureido-functional organosilicon compound. Also, alkylation or methylolation of one or both of the R' groups can be performed on the amino-functional organosilicon compound in which both R' groups are hydrogen or on the ureido-functional organosilicon compound in which both R' groups are hydrogen.

This invention is primarily directed to improvements in foundry sands and foundry cores and molds made therefrom. The foundry sands useful in the present invention are conventional foundry sands such as silica sands having a high silica content, for example a silica content of at least 80% by weight. Examples of such foundry sands are (1) white silica sands such as Wedron White Silica sand, (99.8% by weight silica), Ottawa White Silica sand (99.8% silica), Minnesota White Silica sand (98.5% silica); (2) lake sands, such as Port Crescent sand (95.0% silica), Manley 20KK sand (91.9% silica), Nugent Lake sand (94.2% silica), Lake Shore sand (93.5% silica); and (3) bank sands such as Juniada Bank sand (90.2% silica). Thse foundry sands normally have a Grain Fineness Number (GFN) of about 50 to 90, as determined by the standard AFS method.

Other inorganic oxides or fillers can be bound by the binding agents pursuant to this invention and they include any suitable fibrous or particulate inorganic substrate. At the time of mixing the binding agent with the fillers, the fillers may be in the form of particles, spherical or approximately isometric, or they may be in the form of plates or needles (fibers). The size of the filler particles is not critical, any of the conventionally used fillers being suitable in this respect. Among the specific fillers which may be used in the present invention are asbestos, ground glass, kaolin and other clay minerals, silica, calcium silica, magnesium oxide, barium carbonate, barium sulfate (barytes), metal fibers and powders, glass fibers, refractory fibers, non-reinforcing carbon blacks, titanium dioxide, mica, talc, chopped glass, alumina, quartz, wollastonite (calcium silicate), and inorganic coloring pigments.

The curable binder useful in the binding agent compositions of this invention are polymerizable or thermosetting to form three-dimensional structures and are capable of binding the inorganic oxide or filler into a shaped mass. Included as examples of suitable curable binders are the foundry binders or hardenable resins which when used with the above ureido-functional silicon compounds of this invention show improved strength or resistance to humidity in the foundry core. Generally these foundry binders are the phenolic/polyisocyanate binder systems such as described in U.S. Pat. No. 3,409,579; furan binder systems such as described in U.S. Pat. No. 3,346,534; oil modified polyol/polyisocyanate binder systems such as described in U.S. Pat. No. 3,255,500; and phenolic and urea/phenolic resin binder systems such as described in U.S. Pat. Nos. 3,404,198 and 3,306,864.

Further illustrative of resins which can be effectively bonded include the thermosetting resins, such as the phenol formaldehyde resins, melamine-formaldehyde resins, alkyd resins, polyurethane resins, epoxy resins, and the like.

It is quite surprising that cold-setting resins, such as phenol-formaldehyde resins, for example, which contain ureido-functional organosilicon compounds pursuant to this invention undergo little or no loss of their ability to adhere to fillers or inorganic oxide materials, the absolute adhesivity of these binding agents being equal to or in some cases even greater than that of conventional aminosilanes coupling agents. The stability of ureido-functional organosilicion compounds in cold setting-resins was unexpected and applies to those cases where none or one or more or all of the hydrogen atoms of the ureido group $H_2NC(O)NH$— are substituted by an alkyl group or aryl group.

More broadly, the invention can be applied to substantially any polymeric material in which improved adhesion to fillers or inorganic oxides is desired, including, for example, any of the rubbers, resins or plastics with which fillers, e.g., inorganic oxides, are conventionally employed. Such polymers include natural rubber; synthetic rubbers such as styrene-butadiene rubber; ethylene-propylene terpolymer rubber; urethane rubbers; polyolefins such as polyethylene, polypropylene, and polyisobutylene; poly-acrylonitrile; polybutadiene; copolymers of butadiene and acrylonitrile; polystyrene; poly(styreneacrylonitrile); copolymers of styrene with butadiene and acrylonitrile; copolymers of ethylene with propylene or butene-1 or vinyl acetate or maleic anhydride; polycarbonate resins; phenoxy resins, polyvinyl chloride; copolymers of vinyl chloride with vinyl acetate or other vinyl esters; polyvinyl acetate; linear polyesters; polyvinyl acetals; polyvinylidene chloride; copolymers of vinylidene chloride with vinyl chloride and acrylic acid; poly(methyl methacrylate); superpolyamides, e.g. nylon; polysulfones; allyl resins such as a polymer of diallyl phthalate; epoxy resins, phenolic resins; silicone resins; polyester resins including alkyd resins; poly(vinylacetate-vinyl chloride); poly(vinylidene chloride); thermoplastic polyurethanes; thermoplastic polyhydroxy ethers; thermoplastic polyesters; poly(vinyl chloride-maleic anhydride); and others. Preferred polymeric matrices are the thermosetting or curable resins, such as the hardenable foundry sand resins as described above, and the like.

The proportions of ureido-functional organosilicon compound and curable binder in the novel binding agent compositions of this invention can be varied over a wide range. For example, the novel compositions can contain from about 0.01 to about 5, preferably about 0.05 to about 2, weight parts of ureido-functional organosilicon compound per 100 weight parts of curable binder. The proportions of binding agent composition and sand used in making the novel foundry sand compositions of this invention can be varied over a wide range and are generally the same respectively as the proportions of coupling agent and sand conventionally employed in the art. While the ureido-functional orgaosilicon compounds can be employed undiluted, it usually is more convenient to employ them as solutions, e.g., 25 to 95%, in suitable solvents such as methanol, ethanol, isopropanol and the like because such solutions are easier to handle and disperse in the curable binder.

DETAILED DESCRIPTION OF THE INVENTION

The following Examples are presented. The numbered Examples represent the present invention; the lettered Examples do not represent this invention and are for comparison purposes. Temperatures given are in °C. unless otherwise stated. The following designations used in the Examples and elsewhere herein have the following meanings:

Me: methyl group
lbs/in$^2$ or psi: pounds per square inch
Et: ethyl group
%: percent by weight unless otherwise specified
wt %: weight percent
cc: cubic centimeter
gms: grams
wt: weight
parts: parts by weight unless otherwise indicated
pts: parts by weight unless otherwise indicated

EXAMPLE 1

Preparation Of
$NH_2C(O)NHC_2H_4NHC_3H_6Si(Me)(OMe)_2$—Compound A

Into a 250 cc, 3-neck round bottom flask equipped with distillation head, mechanical stirrer, thermometer with thermo-watch and nitrogen atmosphere, was charged 70.0 gms $NH_2C_2H_4NHC_3H_6Si(Me)(OMe)_2$ (Compound B) plus 25.5 gms methyl carbamate plus 0.10 gms dibutyl tin oxide. The reaction mixture was heated at 105° C. for about 15 hours. Amine titration was used to follow the extent of the reaction. The reaction was stopped at 93% completion. The product was stripped of methanol on a Rota-evaporator. The structure of the product as Compound A was confirmed by $^{13}C$ nuclear magnetic resonance spectroscopy (NMR). In addition to the structure given above for Compound A, $^{13}C$ NMR suggested the formation of a small amount of cyclic structure. A 50 wt.% solution of the Compound A product in methanol was prepared.

EXAMPLE 2

Preparation Of
$NH_2C(O)NHCH_2CH(CH_3)C_2H_4Si(Me)(OEt)_2$—Compound C

Into a 250 cc, 3-neck round bottom flask equipped with distillation head, mechanical stirrer, thermometer with thermo-watch and nitrogen atmosphere, was charged 60.0 gms $NH_2CH_2CH(Me)C_2H_4Si(Me)(OEt)_2$ (Compound D) plus 24.4 gms ethyl carbamate plus 0.10 gms dibutyl tin oxide. The reaction mixture was heated at 105° C. for about 15 hours. Amine titer showed 93% completion. The product was stripped of ethanol on a Rota-evaporator. The structure of the product as Compound C was confirmed by $^{13}C$ nuclear magnetic resonance spectroscopy. A 50 wt. % solution of the product Compound C in methanol was prepared.

EXAMPLE 3

Compound E

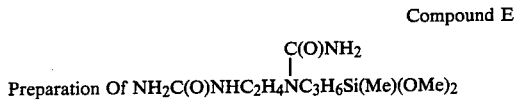

Preparation Of $NH_2C(O)NHC_2H_4NC_3H_6Si(Me)(OMe)_2$

Into a 250 cc, 3-neck round bottom flask equipped with distillation head, mechanical stirrer, thermometer with thermo-watch and nitrogen atmosphere, was charged 70.0 gms Compound B plus 51.0 gms methyl carbamate plus 0.12 gms dibutyl tin oxide. The reaction mixture was heated for about 15 hours at 105° C. Amine titer showed 86% completion. The product was stripped of methanol on a Rota-evaporator. The product was an orange viscous liquid. A 50 wt. % product/methanol solution was prepared. The structure of the product as given above for Compound E was confirmed by $^{13}C$ NMR; however, there were 1 or 2 unidentifiable smaller amounts of by-products present.

EXAMPLES 4–6, A AND B

Five foundry sand compositions were prepared containing the ingredients and amounts of same given in Table 1 below. In Examples 4, 5 and 6, 0.19 millimole of Compound A, C and E, respectively, were used in the composition and in Example B, 0.19 millimole of a commercial coupling agent, A-1160, having the formula $NH_2C(O)NHC_3H_6Si(OEt)_3$ was used. Example A was a control and no coupling agent was used.

TABLE 1

| Foundry Sand Formulation | |
|---|---|
| Ingredient | Grams |
| AFS Testing Sand 50–70 | 1500.00 |
| Phenolic Binder* | 27.90 |
| Catalyst, Toluene Sulfonic Acid | 7.00 |

TABLE 1-continued

| Foundry Sand Formulation | |
|---|---|
| Ingredient | Grams |
| $H_2O$** | 0.75/1.50 |

*1.9% commodity resin based on sand weight. Resin is a commercial phenolic foundry resin supplied by Borden Chemical and identified as Thor F.B. 142 without silane coupling agent. 25% catalyst based on commodity resin.≠**Due to extreme variation (35–95% RH) in humidity during these preparations, the formulations had to be adjusted accordingly. On dry days (<50% RH) 1.5 gms $H_2O$ was required and on humid days (>50% RH) 0.75 gms of $H_2O$ was required to ensure uniform processing parameters and consistent control values.

In Examples B, 4, 5 and 6, 0.19 millimole of the silane coupling agent was added to the 27.9 grams of the phenolic binder and the resulting blend was stirred with a magnetic stirrer for 2 to 4 hours at room temperature. A portion of each resulting mixture was evaluated initially using the procedure described hereinafter and the remaining portion of each mixture was allowed to age for one month at room temperature and then evaluated.

In evaluating each mixture of Examples B, 4, 5 and 6 and in evaluating the control Example A, 1500 gms of sand were charged to the mixing bowl. While mixing at slow speed the required amounts of water and catalyst were added, separately, via syringe and mixed for two minutes. The resin phenolic binder (Example A) or phenolic binder/silane coupling agent mixture (Examples B, 4, 5 and 6) was added via syringe and mixing carried out for an additional two minutes. Immediately following completion of mixing, the molds were filled with the resulting sand mixtures, heaping full without compacting. The sand mixture was then pressed in firmly with the #14 rubber stopper. Additional sand mixture was then heaped above the mold and smoothed off with a trowel. The resulting tensile specimens were allowed to stand for 24 hours after preparation and then tested. The tensile specimens were tested for tensile strength using a jig designed for testing briquets (ASTM C-190-63). The cross-head speed was 0.2 inches/minute. The tensile strengths, initially and after one month age, of the phenolic binder/silane coupling agent mixtures (Examples B, 4, 5 and 6) and the tensile strengths for the control (Example A) are given in Table 2 below.

TABLE 2

| Ex. No. | Coupling Agent | Tensile Strength (lbs/in²) | |
|---|---|---|---|
| | | Initial | 1-Month Age |
| A | Control (no coupling agent) | 220 | 220 |
| B | A-1160 $NH_2\overset{O}{\overset{\|}{C}}NHC_3H_6Si(OC_2H_5)_3$ | 295 | 215 |
| 4 | Compound A | 290 | 290 |
| 5 | Compound C | 310 | 285 |
| 6 | Compound E | 335 | 285 |

The test results given in Table 2 prove the superior performance stability of each of the silane coupling agents of this invention, namely, Compounds A, C and E, as compared to the control (Example A) and the state-of-the-art silane coupling agent (Example B).

What is claimed is:

1. In a binding agent composition for inorganic oxides comprising a curable binder and an organosilicon coupling agent, the improvement wherein said organosilicon coupling agent is a siloxane having, per molecule, two silicon-bonded hydroxyl groups or two silicon-bonded hydrolyzable or condensible groups selected from the group consisting of alkoxy, acyloxy, amino and haloalkoxy and at least one silicon-bonded group of the formula [R'HNC(O)]$_n$—R— wherein R is an aliphatic radical containing at least one nitrogen atom, hydrogen and at least five carbon atoms wherein at least one nitrogen atom therein is bonded to each (R'HNCO)— to form (R'HNCON<)

at least one free valence of (R'HNCON<)

is bonded to an alkylene carbon atom of R, any other free valence of (R'HNCON<)

is bonded to a member selected from the group consisting of hydrogen, alkyl, aryl, cycloalkyl and aralkyl, any nitrogen atom in R is separated from silicon by at least three sequentially joined carbon atoms; R' is hydrogen, alkyl having 1 to 8 carbon atoms or methylol; and n is at least one; and any remaining free valence of silicon is bonded to oxygen which in turn is bonded to another silicon atom to form therewith the siloxane.

2. Binding agent as claimed in claim 1 wherein said siloxane is a disiloxane, a trisiloxane, a tetrasiloxane or a pentasiloxane.

3. Binding agent as claimed in claim 2 wherein said siloxane is a cyclic tetrasiloxane.

4. In a binding agent composition for inorganic oxides comprising a curable binder and an organosilicon coupling agent, the improvement wherein said organosilicon coupling agent has the formula:

H$_2$NC(O)NHC$_2$H$_4$NHC$_3$H$_6$Si(Me)(OMe)$_2$.

5. In a binding agent composition for inorganic oxides comprising a curable binder and an organosilicon coupling agent, the improvement wherein said organosilicon coupling agent has the formula:

$$\underset{H_2NC(O)NHC_2H_4\overset{|}{N}C_3H_6SI(Me)(OMe)_2.}{C(O)NH_2}$$

6. In a foundry sand composition containing foundry sand, a binding agent including a hardenable resin and an organosilicon compound coupling agent, and a catalyst for said hardenable resin the improvement wherein said binding agent is the binding agent defined in claim 4.

7. Foundry sand composition as claimed in claim 6 wherein said binding agent is the binding agent defined in claim 2.

8. In a foundry sand composition containing foundry sand, a binding agent including a hardenable resin and an organosilicon compound coupling agent, and a catalyst for said hardenable resin the improvement wherein said binding agent is the binding agent defined in claim 5.

9. Foundry sand composition as claimed in claim 6 wherein said binding agent is the binding agent defined in claim 3.

* * * * *